United States Patent
Vuillemot

(10) Patent No.: US 7,217,131 B2
(45) Date of Patent: May 15, 2007

(54) METHOD FOR DENTAL RESTORATION AND KIT

(76) Inventor: William C. Vuillemot, 11460 Hidden Spring Trail, DeWitt, MI (US) 48820

( * ) Notice: Subject to any disclaimer, the term of this patent is extended or adjusted under 35 U.S.C. 154(b) by 163 days.

(21) Appl. No.: 10/998,320

(22) Filed: Nov. 26, 2004

(65) Prior Publication Data
US 2006/0115792 A1 Jun. 1, 2006

(51) Int. Cl.
*A61C 5/00* (2006.01)
*A61C 9/00* (2006.01)

(52) U.S. Cl. .......................... 433/215; 433/36; 433/37

(58) Field of Classification Search ............... 433/215, 433/223, 34, 36, 37, 39
See application file for complete search history.

(56) References Cited

U.S. PATENT DOCUMENTS

| | | | |
|---|---|---|---|
| 3,808,687 A | 5/1974 | Millet | |
| 3,987,545 A | 10/1976 | Kennedy | |
| 4,080,736 A | 3/1978 | Kennedy | |
| 4,129,946 A | 12/1978 | Kennedy | |
| 4,172,323 A * | 10/1979 | Orlowski | 433/180 |
| 4,368,040 A * | 1/1983 | Weissman | 433/36 |
| 4,431,421 A * | 2/1984 | Kawahara et al. | 523/115 |
| 5,192,207 A | 3/1993 | Rosellini | |
| 5,332,390 A | 7/1994 | Rosellini | |
| 5,348,475 A * | 9/1994 | Waknine et al. | 433/215 |
| 5,775,913 A | 7/1998 | Updyke et al. | |
| 5,803,737 A * | 9/1998 | Lyalin | 433/223 |
| 5,975,906 A * | 11/1999 | Knutson | 433/226 |
| 5,984,682 A | 11/1999 | Carlson | |
| 6,299,449 B1 * | 10/2001 | Carlson | 433/180 |
| 6,479,592 B2 | 11/2002 | Rheinberger et al. | |
| 6,691,764 B2 * | 2/2004 | Embert et al. | 164/4.1 |
| 6,769,913 B2 | 8/2004 | Hurson | |
| 2002/0119424 A1 * | 8/2002 | Margeas et al. | 433/215 |
| 2003/0069326 A1 | 4/2003 | Stangel et al. | |
| 2004/0167246 A1 | 8/2004 | Subelka et al. | |
| 2004/0202983 A1 * | 10/2004 | Tricca et al. | 433/215 |
| 2005/0175965 A1 * | 8/2005 | Craig et al. | 433/215 |

* cited by examiner

*Primary Examiner*—Ralph A. Lewis
(74) *Attorney, Agent, or Firm*—Ian C. McLeod; Steven E. Merritt

(57) ABSTRACT

Methods and kits of materials and supplies for forming a dental prosthesis by an injection molding process in situ in a patient's mouth so as to correct the imperfect teeth of the patient's dentition. The imperfect teeth are corrected by injection molding the dental prosthesis in situ in the patient's mouth using a mold of a corrected model of the patient's dentition placed over the imperfect teeth. Adjacent teeth are covered with a polymer release material prior to injection molding of teeth to be corrected, such that the teeth to be corrected have at least one tooth between them draped with the polymer release material to provide a space adjacent to each of the corrected teeth. The corrected teeth are then covered with the polymer release material in a second round of treatment to complete the procedure on the remaining teeth.

23 Claims, 7 Drawing Sheets

METHOD FOR DENTAL RESTORATION AND KIT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION (1) Field of the Invention

The present invention relates generally to dental prosthesis, and more particularly to methods of forming dental prosthesis. Specifically, the present invention relates to methods of forming dental prosthesis in situ in a patient's mouth by injection molding using a mold of a corrected model of the patient's dentition.

(2) Description of the Related Art

U.S. Pat. No. 3,808,687 to Millet teaches pontics with a rigid core formed of a plastic material such as acrylic, lucite, plexiglass or other hard material, and detachable cap formed of a flexible plastic such as polyethylene which have the external contours of a natural tooth. The external configuration of the cap is substantially the same as the porcelainized portion of the restoration to be formed. The pontics are used for creating an investment mold for casting a metal frame of gold or other suitable materials to which porcelain is applied. The dental restoration is then fit into the patient's mouth.

U.S. Pat. No. 3,987,545 to Kennedy teaches methods for forming a temporary dental prosthesis as a bridge in situ in a patient's mouth for restoration of missing or broken teeth. The method utilizes a positive model of the patient's mouth which is corrected to the desired size and shape of the teeth to be restored. An elastomeric mold is formed using the model as a pattern which is fitted over the patient's jaw. A self-curing liquid resin is drawn into the cavity by vacuum across the bridge to form the dental prosthesis which is removed and then cemented in place. This requires that a good seal be provided between the jaw and the mold.

U.S. Pat. No. 4,080,736 also to Kennedy teaches a method and apparatus for forming a dental prosthesis for restoration of a patient's teeth. An elastomeric mold and a hard model are secured together to form an assembly with a mold cavity within. The assembly is placed in a vacuum chamber to produce a vacuum inside the chamber and the mold. When a connection between a source and the assembly is opened a liquid material is pushed into the mold cavity to form the prosthesis, which is then installed in the patient.

U.S. Pat. No. 4,129,946 to Kennedy teaches hollow dental crown forms, preferably co-polyester plastics, having the shape of a natural tooth for holding and shaping composite resin material applied to a tooth which requires restoration. A tab which provides a gripping handle is formed at the base of the crown form, and a flange is formed around the base of the crown form. The crown is then installed in the patient.

U.S. Pat. Nos. 5,192,207 and 5,332,390 to Rosellini teach crowns or replacement teeth and methods of production thereof. The crown or replacement teeth are formed by filling a transparent shell tooth with a light setting resin and disposing the filled transparent shell tooth onto a prepared tooth of a patient. The filled shell tooth is illuminated to set the resin and bond it to the shell tooth form. Polishing and shaping are then done in situ to form the crown.

U.S. Pat. No. 5,775,913 to Updyke et al. teach a method of making caps of eight different sizes for each of a persons teeth. The caps are preferably prepared from quartz or silicon dioxide filled acrylic materials. The caps can be placed over a prepared tooth and exposed to ultraviolet light to form the solid capped tooth.

U.S. Pat. No. 5,984,682 to Carlson teaches permanent composite dental bridges constructed either in situ or ex situ. The material is applied in the in situ process between abutment teeth and wings formed from the composite material are attached to surfaces of the abutment teeth before curing. These steps are successively repeated until a dental bridge is form within the patient's mouth. A gingival stent is used as a platform upon which the composite laminations are formed, and is removed after the formation of the bridge prior to contouring and finishing of the bridge.

U.S. Pat. No. 6,769,913 to Hurson discloses an impression cap and methods of taking dental impressions in a patient's mouth by injecting an impression material into an inner cavity of the impression cap. The impression cap is then removed from the patient's mouth for the fabrication of a dental restoration.

While the related art teach various methods of forming dental prosthesis in situ, there still exists a need for an improved method of forming injection molded dental prosthesis in situ in a patient's mouth.

OBJECTS

Therefore, it is an object of the present invention to provide an improved method of forming dental prosthesis in situ in a patient's mouth by injection molding.

It is further an object of the present invention to provide a kit of materials, supplies and instructions for correcting the teeth of a patient by the provided methods.

These and other objects will become increasingly apparent by reference to the following description.

SUMMARY OF THE INVENTION

The present invention provides a method for restoring teeth in need of restoration in a patient by providing a fluid dental restoration polymer composition which is curable on prepared teeth to be restored and curing the composition to provide the composition bonded to the prepared teeth in providing restored teeth, the improvement which comprises: (a) preparing selected teeth to be restored for bonding with the fluid polymer composition; (b) covering teeth which are not to be restored with a polymer release material; (c) fitting a clear polymer composition mold over the teeth to be restored and the teeth not to be restored, which mold provides a closed space to be filled between the teeth to be restored and the mold which defines a shape of the restored teeth, wherein the mold has an inlet port for injection of the fluid polymer composition and an outlet port for removing any excess air and/or excess fluid polymer resulting from the injection; (d) injection molding the fluid polymer composition into the mold to fill the space in the mold with the covered teeth and the teeth to be restored; (e) curing the fluid polymer composition onto the teeth to be restored in the clear polymer composition mold; (f) removing the mold from the teeth and the tape from the covered teeth to provide the restored teeth in the patient; and (g) optionally finishing exposed surfaces of the restored teeth, if necessary.

In further embodiments of the method, the polymer release material is polytetrafluoroethylene. In still further embodiments the polymer release material is in tape which is preferably about 1.5 cm wide and about 0.2 mm thick. In still further embodiments the clear polymer composition mold comprises a clear plastic tray filled with a cured clear plastic polymer composition and which is derived from a prepared model with the teeth as they will be restored in the patient, and wherein the inlet and outlet ports are drilled into the mold. In further embodiments a dental cast is prepared from an impression of the teeth to be restored, then a dental stone model is prepared, and then the stone model is modified to simulate the restored teeth as they will be restored. In further embodiments the fluid polymer composition is cured with light. In still further embodiments the fluid polymer composition is cured with ultraviolet light of about 465 nm to about 480 nm. The activating ultraviolet light of 465 nm to 480 nm is directed throught the clear, light-transmitting mold for the purpose of hardening or curing the light-sensitive fluid polymer composition for the dental restoration. In further embodiments of the method, the dental restoration fluid polymer composition is a particle filled and pigmented poly(acrylicacid)polymer containing a curing agent activated by light. In still further embodiments the dental stone model is modified with a wax shaped to simulate the restored teeth. In further embodiments of the method, in step (a) prepared teeth are etched with an acid and then coated with a primer and bonding agent for bonding the dental restoration fluid polymer composition to the prepared teeth. In preferred embodiments the bonding agent comprises methacrylate ester monomers and the primer comprises alkyl dimethacrylate resins. In further embodiments of the method alternate of the teeth to be restored are restored in two or more repetitions of the steps (a) to (e).

The present invention provides a kit for restoring teeth by injection molding and curing a dental restoration fluid polymer composition onto teeth in need of restoration in a patient which comprises: (a) mold forming means for providing a clear polymer mold which mold provides a closed space to be filled with the fluid polymer composition between the teeth to be restored and the mold and which defines a shape of the restored teeth, wherein the mold has an inlet port for injection of the fluid composition polymer and an outlet port for any excess air and/or excess fluid polymer; (b) a polymer release material for covering teeth which are not to be restored in the clear polymer mold; and (c) a fluid dental restoration polymer composition curable by light for bonding to the teeth to be restored.

In further embodiments of the kit the fluid polymer composition comprises particles and pigment in a poly(acrylicacid)polymer composition containing a curing agent activated by light. In still further embodiments, the kit contains in addition an acid etchant for the teeth to be restored, a primer for these teeth and a bonding agent for bonding the fluid polymer composition to these teeth. In preferred embodiments the bonding agent comprises methacrylate ester monomers and the primer comprises alkyl dimethacrylate resins. In still further embodiments, the kit in addition can optionally contain a ceramic powder for forming a dental stone impression model of the prepared teeth of the patient and a modeling material such as a dental wax for modifying the dental stone model to simulate the restored teeth in the patient. In still further embodiments the polymer release material is a polytetrafluoroethylene tape. In preferred embodiments, the polymer release material is a polytetrafluoroethylene tape which is about 1.5 cm wide and about 0.2 mm thick. In further embodiments of the kit containing the clear plastic tray, a curable clear polymer composition to provide an impression of a dental cast or model of the teeth to be restored to provide the mold. In further embodiments of the kit, comprising in addition instructions for performing the method steps of Claim 1. In still further embodiments of the kit, comprising in addition instructions for performing the method steps of Claim 1 and wherein the instructions call for restoration of alternate teeth to be restored in two or more of steps (a) to (e).

DETAILED DESCRIPTION OF THE INVENTION

Figure 1:
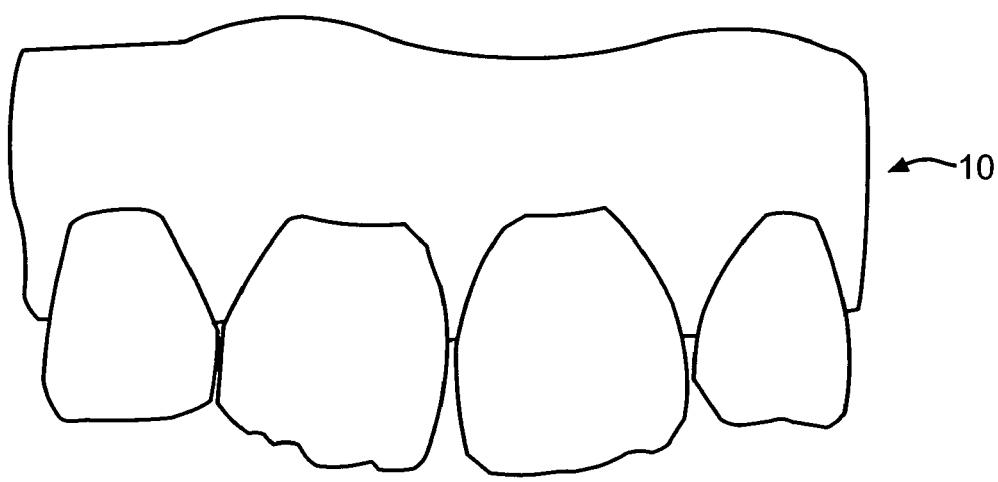
FIG. 1 shows a patient's teeth 10 to be restored.
Figure 2:
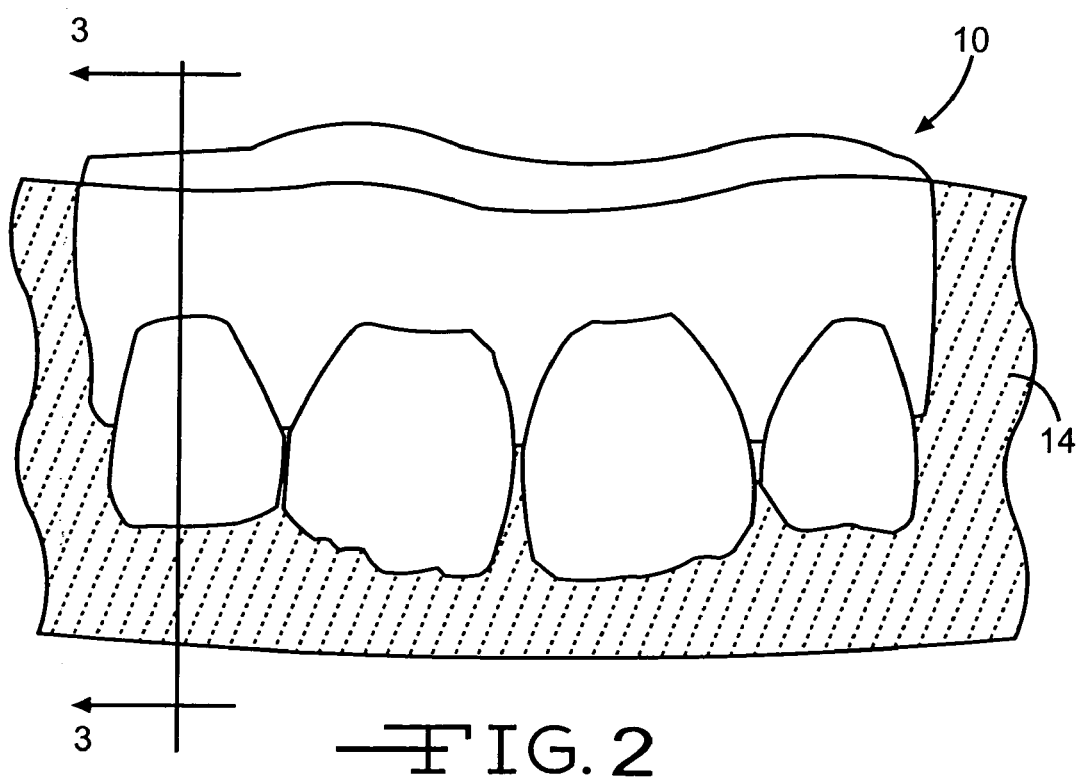
FIG. 2 shows an impression 14 being taken of the current condition of the patient's teeth 10 to be restored.
Figure 3:
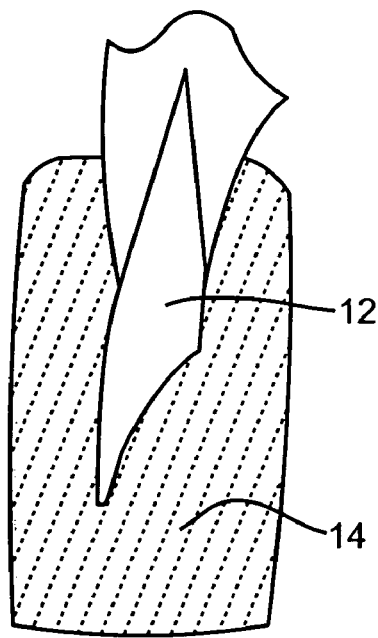
FIG. 3 shows a cross-section of a tooth 12 taken along line 3-3 of FIG. 2.
Figure 4:
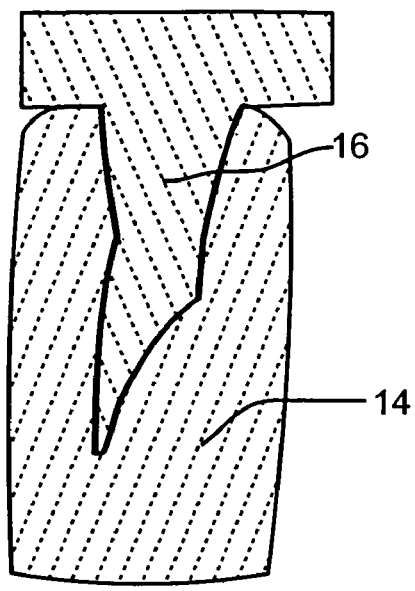
FIG. 4 shows a plaster model 16 cast from the impression 14 taken of the current condition of the patient's teeth.

All patents, patent applications, government publications, government regulations, and literature references cited in this specification are hereby incorporated herein by reference in their entirety. In case of conflict, the present description, including definitions, will control.

The term "polymer release material" as used herein refers to a material such as a tape for wrapping or draping untreated teeth. The material acts as a parting agent, preventing the molded composite from sticking to a surface covered with the material. The term refers to a material including, but not limited to tape such as a pipe thread tape including polytetrafluoroethylene (PTFE) pipe thread tapes. One example of the polymer release material is TEFLON® pipe thread tape (DuPont, Wilmington, Del.).

The term "model" refers to a dental cast commonly referred to as a plaster model or a dental stone model which reflects the current condition of the patient's teeth. Preferably, the model comprises a gypsum die stone. More preferably, the gypsum die stone further comprises a resin including but not limited to acrylic, polyester, urethane or epoxy resins. Most preferably, the gypsum die stone material for the dental model is AMERICAN DIEROCK® resin die stone marketed by American Diversified Dental Systems of Anaheim, Calif.

The term "modeling material" as used herein refers to any material used for the modification of dental models such as dental waxes.

The term "fluid polymer composition" as used herein refers to a flowable material which can be cured to harden the material, including dental composite resins. The fluid polymer composition is preferably curable by exposure to light, however chemical curing is within the scope of the invention. Most preferably, the composition is cured with ultraviolet light of about 465 nanometers (nm) to about 480 nm. One example of a composite resin is HELIOMOLAR® Flow composite (Ivoclar Vivadent, Amherst, N.Y.) which is a monomer matrix of 2,2-bis-4-(3-methacryloxy-2-hydroxypropoxy)-phenylpropane (Bis-GMA), urethane dimethacrylate and decandiol dimethacrylate (40.5 wt %) with highly dispersed silicon dioxide, ytterbiumtrifluoride and copolymer (59 wt %) fillers and additionally catalysts, stabilizers and pigments (0.5 wt %).

The methods of the present invention use common dental materials and supplies in a completely unique and helpful way. This invention will have a profound impact on the way dental restoratives are delivered to patients. Utilizing the methods of the present invention, common dental problems, from simple to complex, can be diagnosed and treated rapidly, and accurately, often at fees lower than comparative options.

The present invention further provides a kit which provides all necessary materials and supplies in a plastic carrying case. The case can be moved from operatory to operatory as needed. The kit also contains all necessary educational materials, including written, video, and CD form for delivery of instruction. The kit provides all necessary contact information for reorder of needed products, and also contacts for technical support.

The present invention enables a dentist to reproduce a diagnostic wax-up, in an exacting manner, directly in a patient's mouth. This enables the performance of complex, comprehensive and sometimes extensive treatment, with superb accuracy and in an exacting manner, at one sitting.

Diagnostic wax-ups have been used for decades, to study ways of restoring damaged or mal-aligned dentitions. Once solutions are arrived at using the wax-up, a treatment plan is formed. The work in the mouth is made to approximate the wax-up, using various conventional methods. These methods include bonding (applying the restoratives directly in the mouth using a sculpting technique, or "free-hand" technique), crown and bridge preps and placement, or applying orthodontic appliances. These various methods can only approximate the diagnostic wax-up, because the work subsequently provided is subject to the dentist's, and/or dental lab technician's interpretations or hands-on manipulations. Prior to the present invention, no way existed to quickly and accurately transfer the exact contours of the wax-up directly to the patient's mouth.

The object of this invention is improving a patient's current dental condition or acquired bite. The current condition, or wants or needs, described by the patient are referred to as the chief complaint. Current condition, or acquired bite may present as one or more of the following: worn tooth surfaces (when areas which are ideally or normally sharp and pointed are flattened or worn down); fractured teeth; severely decayed teeth; discolored or stained teeth; teeth which are too small for the arches and therefore have excess space between them; and mal-positioned or mal-aligned teeth.

Therefore, the desired changes, or restoration of the teeth can be as follows: re-addition of worn surface (which may involve many teeth, and allows the option of "opening the bite"); repair and restoration of fractured teeth; repair and restoration of decayed teeth; covering up of unsightly stains or discolorations; widening of small teeth to close spaces or gaps; and additive or subtractive coronoplasty to improve symmetry and alignment (masking of malposed teeth-giving impression of "instant orthodontics").

Figure 5:
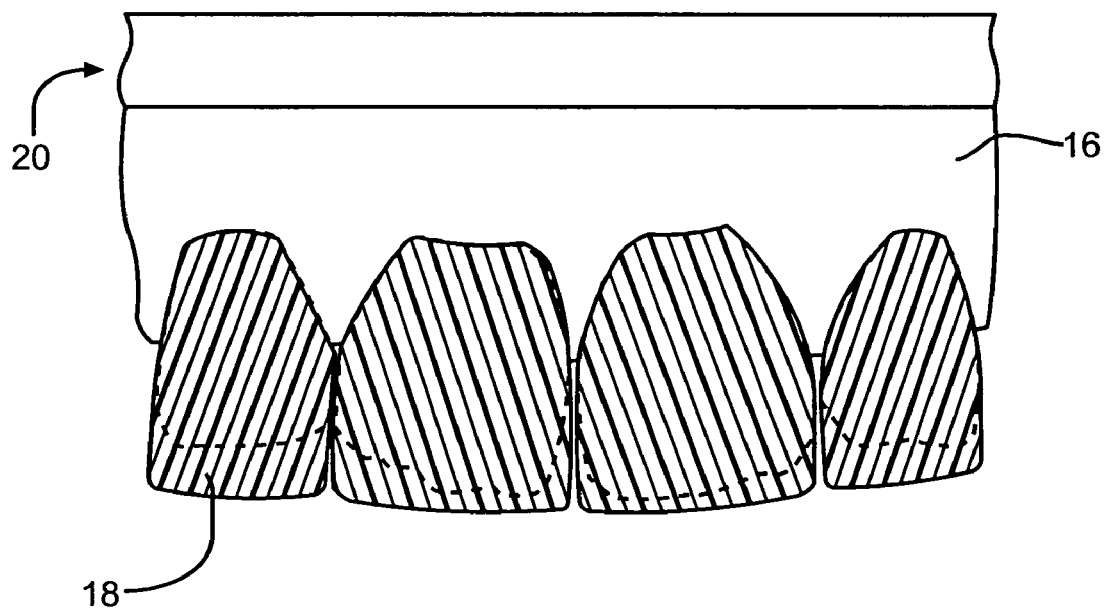
FIG. 5 shows a waxed-up model 20 which is constructed from the plaster model 16 having desired changes made with the addition of dental wax 18.

The following discussion details the procedural steps of the methods of the present invention: A plaster model 16, commonly referred to as a dental stone model, of the patient's teeth 10, exhibiting the current condition is acquired as shown in the sequence of FIGS. 1-4. Preferably, the plaster model comprises a gypsum die stone. More preferably, the gypsum die stone further comprises a resin such as a urethane or an epoxy resin. Most preferably the gypsum die stone material for the plaster model is AMERICAN DIEROCK® resin die stone marketed by American Diversified Dental Systems of Anaheim, Calif. The model is an accurate reproduction of the patient's acquired bite, and demonstrates the chief complaint, which can then be studied carefully. Desired changes are made to the plaster model 16 by addition of dental wax 18 as shown in FIG. 5. The dental wax 18 is heated till flowable, and then "daubed" onto the plaster model 16, with a metal waxing instrument. When the dental wax 18 has cooled, it can be shaped with carving instruments, and polished. A variety of conditions can be improved using the present invention. Examples include fractures, gaps, wear, and rotations and/or malpositions. Care must be taken to ensure that the desired changes are performed on the tooth models in an exacting manner. The transfer technique is highly accurate, and any changes represented by the wax 18 contours, on the plaster model 16, will be reproduced on the teeth in the patient's mouth.

Next, clear plastic impression trays are measured and selected to fit the modified dental plaster model 16. The surface of the trays must be smooth, with no retention holes. Clear polyvinyl siloxane impression material 22 is then injected into the clear trays. A product such as RSVP® polyvinyl siloxane (Cosmodent, Chicago, Ill.) is a good choice of clear impression material.

Figure 6:
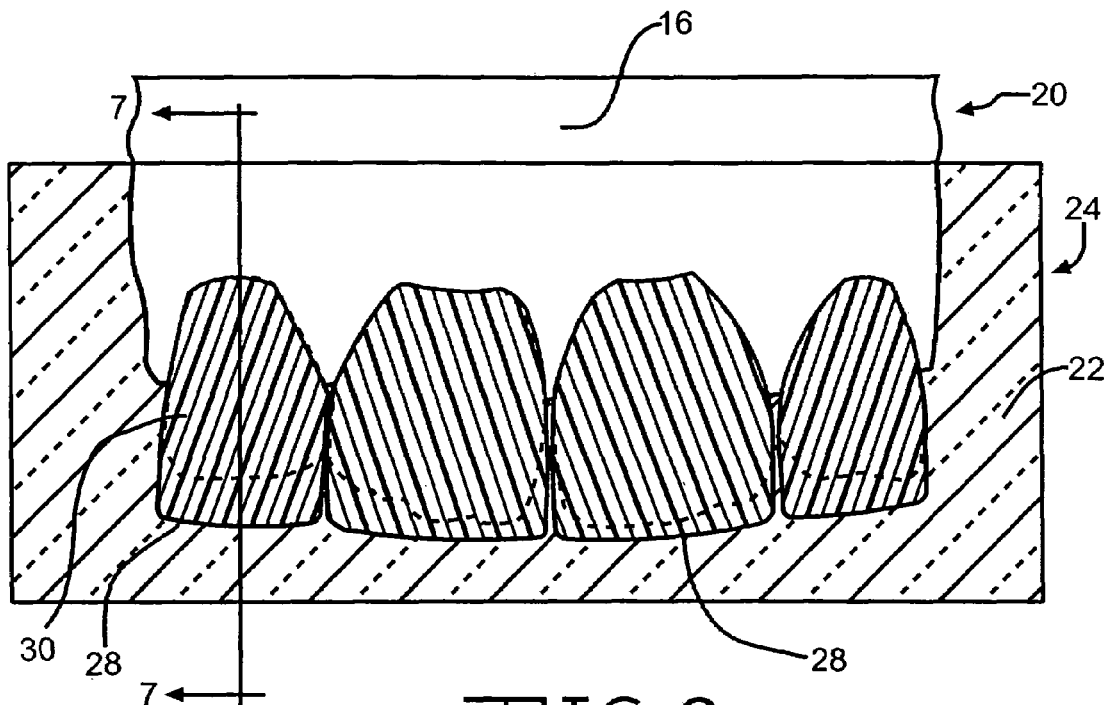
FIG. 6 shows clear impression material 22 which remains over the waxed-up model 20 after removal of the impression tray.
Figure 7:
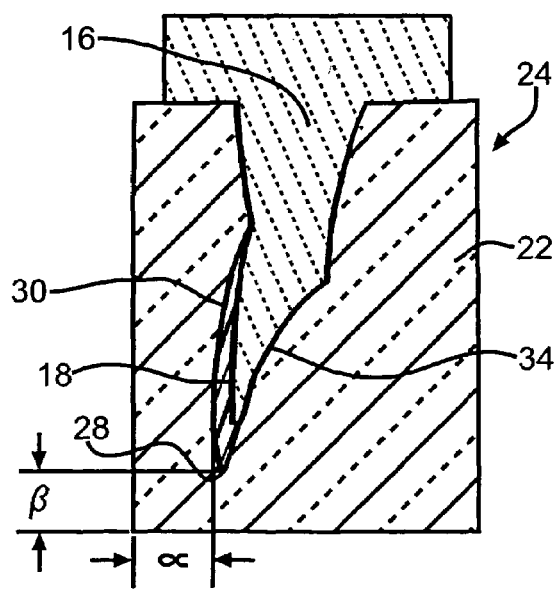
FIG. 7 is a cross-section of the waxed-up model 20 taken along line 7-7 of FIG. 6 showing the mold 24 having desired changes over the plaster model 16 with the dental wax 18 corrections.

The tray full of impression material 22 is inverted over the waxed-up dental stone model 20, and pressed down to entirely cover the tooth and tissue surfaces as shown in FIGS. 6 and 7, thus recording an impression which defines a space 58 reflecting the desired dentition. Prior to the setting, or hardening of the impression material 22, while it remains viscous or plastic, the tray is maneuvered so that a thickness α of approximately two millimeters (mm) of material remains over the buccal surfaces 30 of the teeth, and a thickness β of approximately two millimeters (mm) of clear impression material 22 remains over the incisal surfaces 28 of the teeth. It is fine to have excess material to the lingual or palatal side 34 of the teeth 10. The excess impression material 22 is desired for stiffness and rigidity of the set material 22. The set material 22 will henceforth be referred to as a mold 24. FIG. 6 shows the clear impression material which remains over the waxed-up plaster model after removal of the impression tray which is the mold having the desired changes to the patient's teeth After three minutes, the impression material 22 will be set, or hardened to form the mold 24. The hard, clear impression tray is carefully flexed, and removed from the mold 24. The mold 24 will remain firmly attached to the waxed-up stone model 20. Using a sharp lab knife, for example an exacto-knife, the excess clear impression material 22 is cut away from the waxed-up model 20 at the height of contour (gingival crest) or the buccal mucosa, and lingual and palatal tissues. Allowing the molded edges to extend beyond the teeth and rest on the gingival tissues is desirable and necessary, both for stability of the mold 24 during placement, and the accuracy of the restorative changes near the gum-line.

Figure 8:
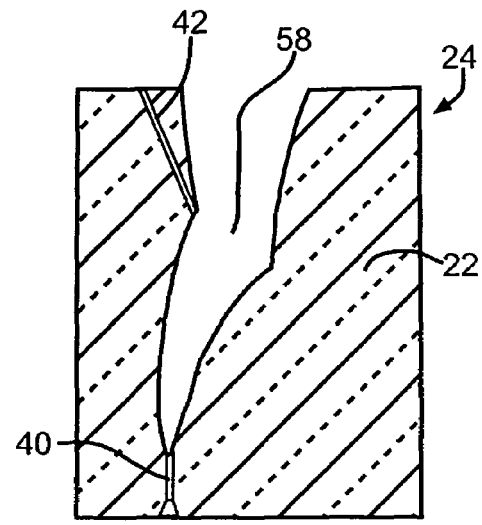
FIG. 8 is a cross-section of the mold 24 taken along line 7-7 of FIG. 6 after removal of the clear impression material 22 from the waxed-up plaster model.

Using fingers and thumbs, the edges of the clear mold 24 are carefully peeled from the waxed-up stone model 20. If caution is exercised, the clear mold 24 can be lifted from the waxed-up stone model 20 with no damage to either the wax 18 or mold 24. The dentist now possesses a clear, see-through mold 24, which is a negative, or impression mold, of the idealized waxed-up model 20. When this mold is placed over the patient's teeth 10, it will snap into place with precision, and fit securely. The patient's teeth 10 will fill the space 58 in the mold 24 exactly, except where wax 18 was placed on the stone model 16. Where wax 18 was placed, a space 58 will exist, either between, over, or around a tooth 12, defined by the inner contours of the mold 24. It is into this space 58 the restorative material, specifically the composite resin 54, will be injected to make the desired changes to the teeth 10. FIG. 8 shows the mold which has been cut to ensure proper thickness on the buccal and incisal aspects of the teeth showing the ingress holes and vent holes which have been cut with a diamond bur.

Figure 9:
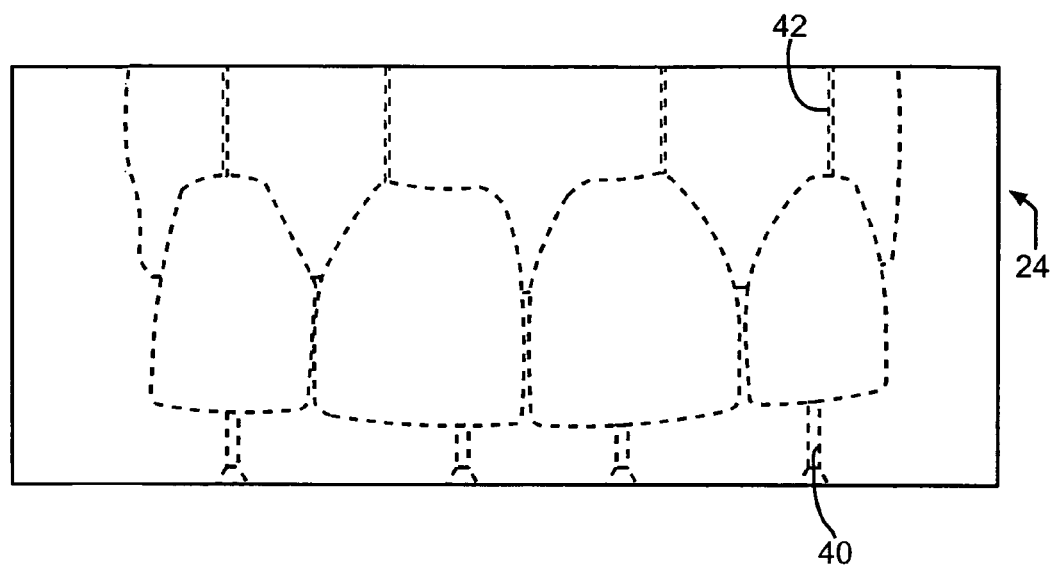
FIG. 9 is the mold 24 having desired changes after removal from the waxed-up model and cutting of the ingress holes 40 and vent holes 42 adjacent to each of the teeth.

An ingress hole 40 must be placed in the mold 24 to allow access for the composite 54 to be injected. A vent 42 must also be placed in the mold 24, to allow air to escape as the restorative is forced into the space 58 through the access of the ingress hole 40. With the tray off the model, the ingress holes 40 for injection and the vents 42 are placed using an air rotor drill motor handpiece and a bur preferably a BRASSELER® #849L 009 diamond bur (Savannah, Ga). One injection ingress hole 40 and vent 42 are required for each tooth 12 to be restored. Any dust or debris from the venting procedure is removed with water rinse and compressed air. The mold 24, as shown in FIGS. 8 and 9, is now ready for use.

Patient Treatment Procedures: The patient is prepared according to normal custom. Anti-anxiety agents, and anesthetics are used as needed. The enamel and dentin tooth surfaces must be prepared for composite bonding according to standard procedures.

Figure 10:
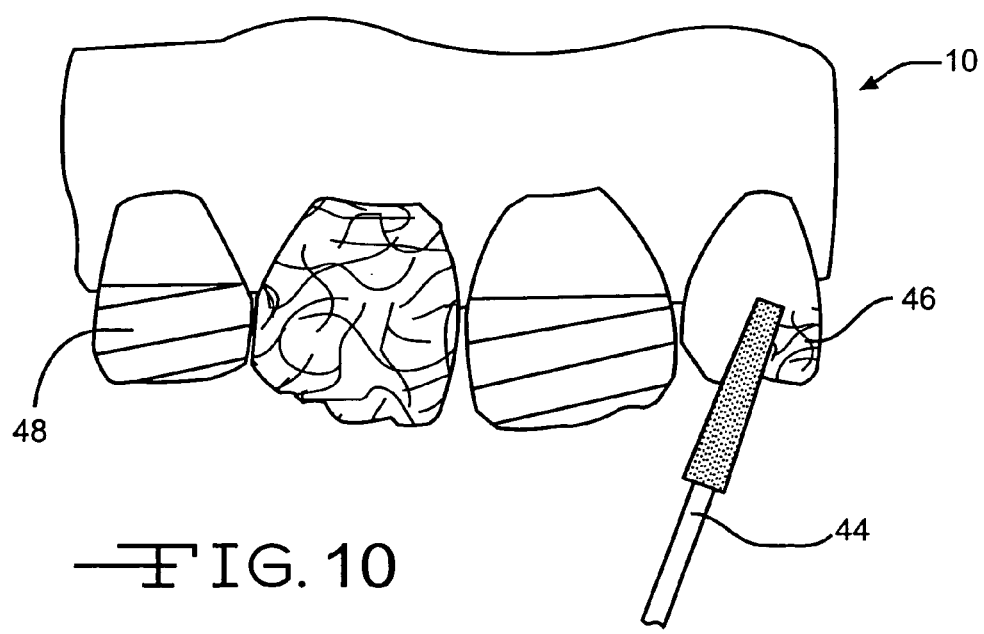
FIG. 10 shows preparation of the patient's teeth 10 by roughening the teeth with a fine diamond bur 44 and covering the teeth with a polymer release material 48.
Figure 11:
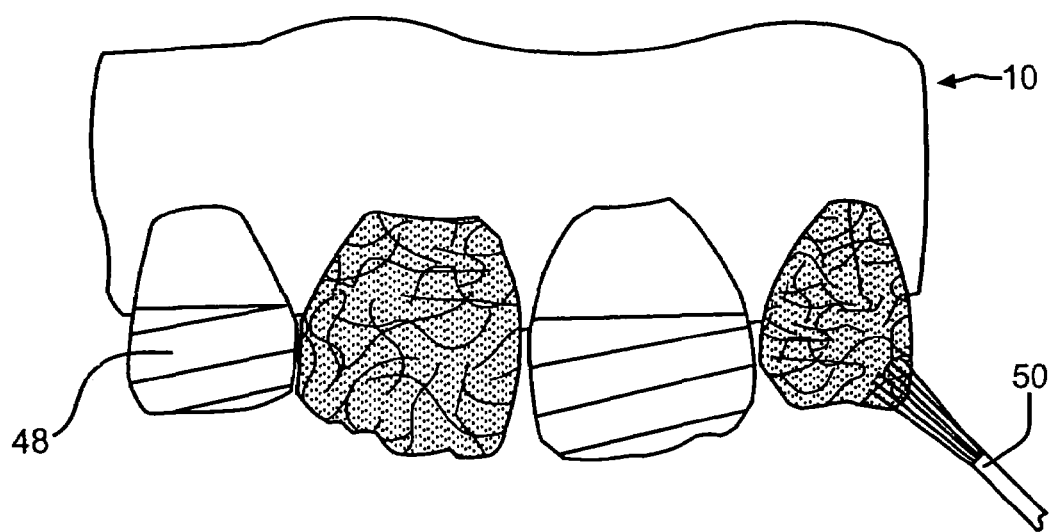
FIG. 11 shows application of a bonding resin primer after teeth have been etched.
Figure 12:
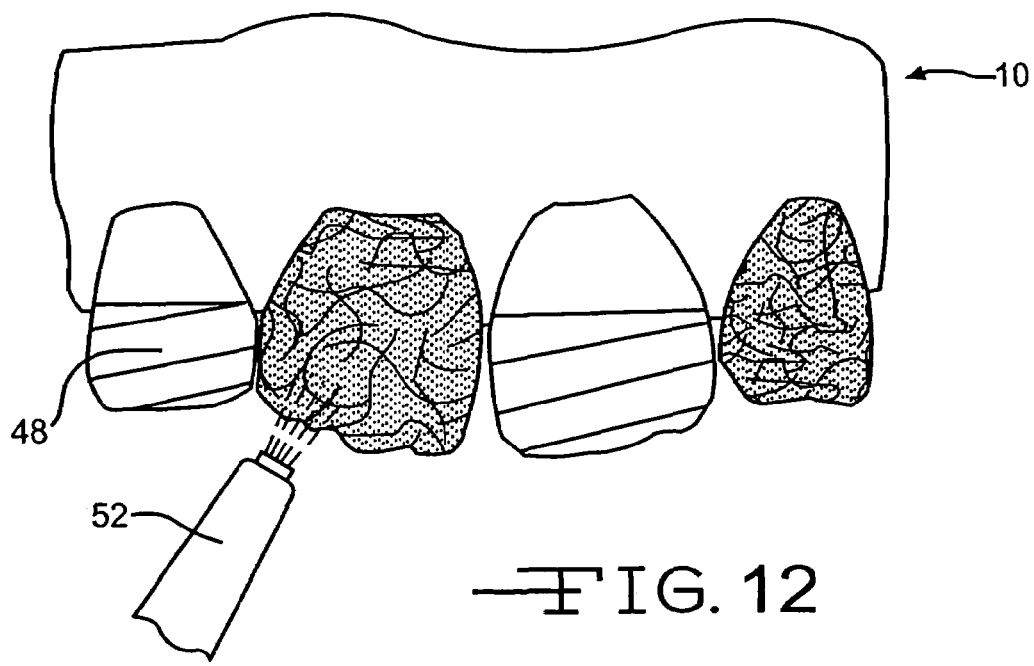
FIG. 12 shows light curing of a bonding agent applied after the bonding resin primer.

A typical procedure is as follows: The teeth 10 are lightly scuffed 46, or roughened with a fine diamond bur as shown in FIG. 10. These surfaces of the teeth 10 are etched, with a twenty second application of 35% phosphoric acid gel, then rinsed with water. The teeth will appear a frosty white color when etched. Thin, non-viscous bonding resin primer is then brushed onto the tooth using brush 50 as shown in FIG. 11. Next, a bonding agent (which is a slightly more viscous resin) is applied and is light 52 cured as shown in FIG. 12. In preferred embodiments the bonding agent comprises methacrylate ester monomers and the primer comprises alkyl dimethacrylate resins. Preferably, the primer and bonding agent are OPTIBOND FL® primer and adhesive marketed by Kerr Corporation, Orange, Calif.

Figure 13:
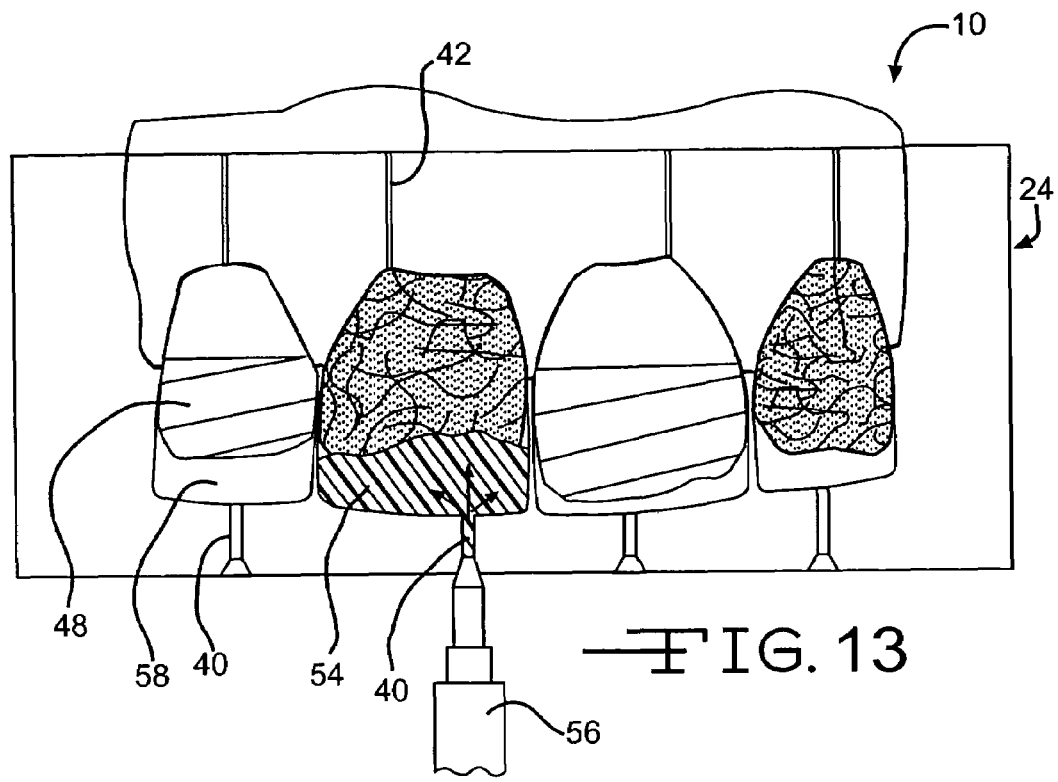
FIG. 13 shows injection of the flowable composite resin 54 with a syringe 56 having a narrow tip.

The best way to restore multiple teeth 10 in a row, is to do every other tooth 12 in two separate applications. That way, the teeth 10 are not fused together by the bonding resins. Teeth not to be bonded in the first application are "draped", or isolated by covering with a polymer release material 48 such as a pipe thread tape. Preferably, the polymer release material 48 is a polytetrafluoroethylene tape. As such, every other tooth will be covered with a wrap of polymer release material 48. The first teeth to be restored will be not covered. Place the mold 24 over the arch, and snap firmly into place. Prior to injection, verify that the tray is seated firmly. Flowable composite resin 54 is now injected, with moderate pressure from the thumb on the composite syringe 56 plunger. FIG. 13 shows injection of the flowable composite resin 54 with the syringe 56 having a narrow tip into the ingress hole 40 over a tooth to be treated after the mold 24 has been seated firmly over the arch in the patient's mouth.

Figure 14:
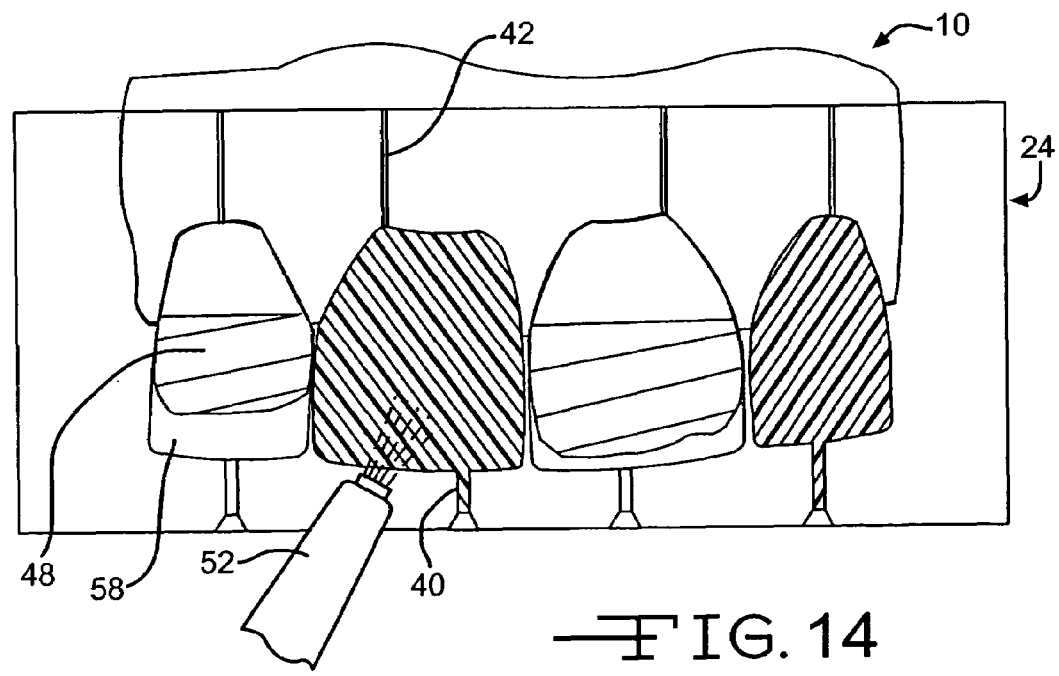
FIG. 14 shows curing of the flowable composite resin using a curing light 52.

It is preferable to use a flowable composite resin 54 to restore with this technique. Many such materials are available for use. Some examples of composite resins are described in U.S. Pat. No. 6,479,592 to Rheinberger et al., U.S. Patent Application Publication No. 2004/0167246 to Subelka et al., and U.S. Patent Application Publication No. 2003/0069326 to Stangel et al. hereby incorporated herein by reference in their entirety. One preferred material is HELIOMOLAR® Flow composite (Ivoclar Vivadent, Amherst, N.Y.). The diameter of the tubing closely approximates the diameter of the BRASSELER® #849L 009 diamond bur used to make the injection ingress holes 40 in the clear mold 34. The syringe 56 tip is placed in a ingress hole 40 directly over a tooth 12 not covered by with polymer release material 48. The composite resin 54 is flowed, or injected by pushing on the plunger with the thumb. The dentist can monitor the progress of the composite resin 54 flow, and stop applying pressure when the composite resin 54 begins to escape from the vent 42. After injection, cure, or harden the resin with electromagnetic energy such as light emitted from a curing light 52 (465-480 nm) for thirty seconds as shown in FIG. 14.

Figure 15:
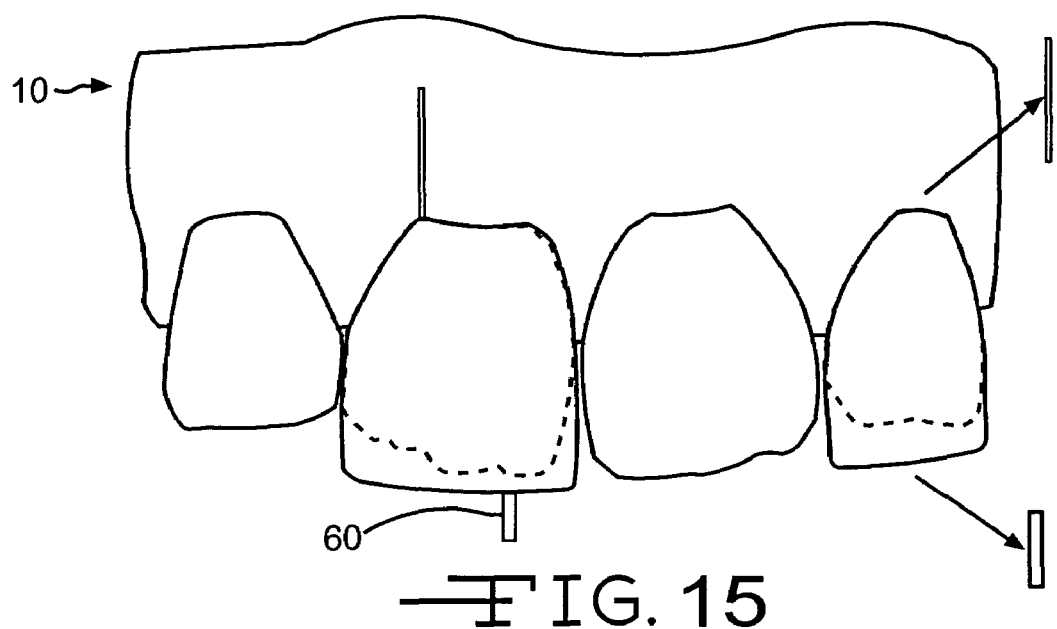
FIG. 15 shows removal of the tray and mold 24, polymer release material 48, and excess resin 60 prior to smoothing and polishing the restored teeth 10.
Figure 16:
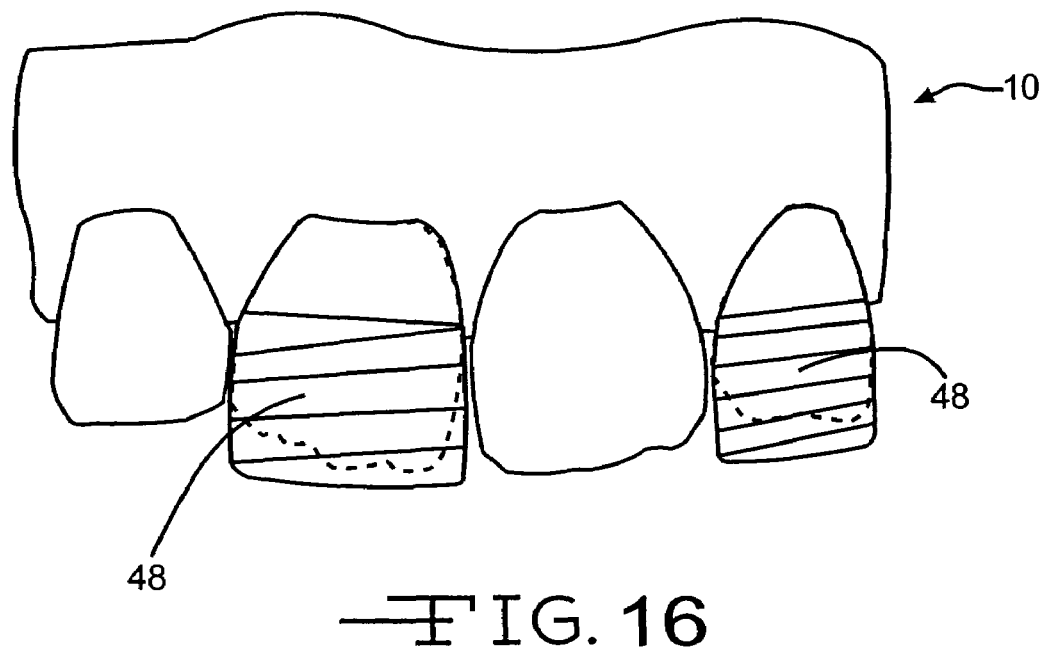
FIG. 16 shows the restored teeth 10 wrapped polymer release material 48 in preparation for a second round of restoration.

Finally, repeat the injection steps of FIGS. 10-15 for each tooth not covered by with the polymer release material 48 in the first application. First, remove the mold. Next, remove the polymer release material 48 and then remove any excess resin, such as flash 60, as shown in FIG. 15. Next, smooth and polish restored teeth. Now, place polymer release material 48 over the restored teeth. FIG. 16 shows the restored teeth wrapped polymer release material 48 in preparation for a second round of restoration similar to the first round shown in FIG. 10 through FIG. 15. The unrestored teeth covered with the polymer release material 48 in FIG. 10 are treated in the second round. Every other remaining tooth will be uncovered, and non-restored. Etch, prime and bond non-restored teeth. Next, place the mold 24 back over dental arch and snap into place. Inject composite resin 54 into remaining non-restored tooth spaces and light cure. Then remove the mold 24 and the polymer release material 48. Afterwards, finish and polish the remaining restorations. Finally, check the occlusion (i.e. the bite) and adjust if needed.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:

1. In a method for restoring teeth in need of restoration in a patient by providing a fluid dental restoration polymer composition which is curable on prepared teeth to be restored and curing the composition to provide the composition bonded to the prepared teeth in providing restored teeth, the improvement which comprises:
    (a) preparing selected teeth to be restored for bonding with the fluid polymer composition;
    (b) covering teeth which are not to be restored with a polymer release material;
    (c) fitting a clear polymer composition mold over the teeth to be restored and the teeth not to be restored, which mold provides a closed space to be filled between the teeth to be restored and the mold which defines a shape of the restored teeth, wherein the mold has an inlet port for injection of the fluid polymer composition and an outlet port for removing any excess air and excess fluid polymer resulting from the injection;
    (d) injection molding the fluid polymer composition into the mold to fill the space in the mold with the covered teeth and the teeth to be restored;
    (e) curing the fluid polymer composition onto the teeth to be restored in the clear polymer composition mold;
    (f) removing the mold from the teeth and the tape from the covered teeth to provide the restored teeth in the patient.

2. The method of claim 1 wherein the polymer release material is polytetrafluoroethylene.

3. The method of claim 2 wherein the polymer release material is in tape which is about 1.5 cm wide and about 0.2 mm thick.

4. The method of claim 1 wherein the clear polymer composition mold comprises a clear plastic tray filled with a cured clear plastic polymer composition and which is derived from a prepared model with the teeth as they will be restored in the patient, and wherein the inlet and outlet ports are drilled into the mold.

5. The method of claim 4 wherein a dental cast is prepared from an impression of the teeth to be restored, then a dental stone model is prepared, and then the stone model is modified to simulate the restored teeth as they will be restored.

6. The method of claim 5 wherein the dental stone model is modified with a wax shaped to simulate the restored teeth.

7. The method of claim 1 wherein the fluid polymer composition is cured with light.

8. The method of claim 7 wherein the fluid polymer composition is cured with ultraviolet light of about 465 nm to about 480 nm.

9. The method of claim 1 wherein the dental restoration fluid polymer composition is a particle filled and pigmented poly(acrylicacid)polymer containing a curing agent activated by light.

10. The method of claim 1 wherein in step (a) prepared teeth are etched with an acid and then coated with a primer and bonding agent for bonding the dental restoration fluid polymer composition to the prepared teeth.

11. The method of claim 10 wherein the bonding agent comprises methacrylate ester monomers and the primer comprises alkyl dimethacrylate resins.

12. The method of claim 1 wherein alternate of the teeth to be restored are restored in two or more repetitions of the steps (a) to (e).

13. The method of claim 1 wherein after step (f) the exposed surfaces of the restored teeth are finished.

14. A kit for restoring teeth by injection molding and curing a dental restoration fluid polymer composition onto teeth in need of restoration in a patient which comprises:
    (a) mold forming means which provides a clear polymer mold which is transparent to light, which cures the restoration fluid polymer which mold provides a closed space to be filled with the fluid polymer composition by injection between the teeth to be restored and the mold and which defines a shape of the restored teeth, wherein the mold has an inlet port for injection of the fluid composition polymer and an outlet port for any excess air and excess fluid polymer composition;
    (b) a polymer release tape material for covering teeth adjacent to the mold which are not to be restored in the clear polymer mold by filling the mold with the polymer adjacent the release material;
    (c) a fluid dental restoration polymer composition curable by light for the curing and the bonding to the teeth to be restored; and
    (d) instructions showing the formation and use of the mold forming means with the release material, the mold, and the polymer as set forth in (a), (b) and (c).

15. The kit of claim 14 wherein the fluid polymer composition comprises particles and pigment in a poly(acrylicacid)polymer composition containing a curing agent activated by light.

16. The kit of claim 15 wherein the kit contains in addition an acid etchant for the teeth to be restored, a primer for these teeth and a bonding agent for bonding the fluid polymer composition to these teeth.

17. The kit of claim 16 wherein the bonding agent comprises methacrylate ester monomers and the primer comprises alkyl dimethacrylate resins.

18. The kit of claim 17 containing the clear plastic tray, a curable clear polymer composition to provide an impression of a dental impression of the teeth to be restored to provide the mold.

19. The kit of claim 16 wherein the kit in addition contains a ceramic powder for forming a dental stone impression model of the prepared teeth of the patient and a modeling material for modifying the dental stone model to simulate the restored teeth in the patient.

20. The kit of claim 14 or 15 wherein the polymer release tape material is a polytetrafluoroethylene tape.

21. The kit of claim 14 or 15 wherein the polymer release material is a polytetrafluoroethylene tape which is about 1.5 cm wide and about 0.2 mm thick.

22. The kit of claim 14 comprising in addition instructions for performing a method for restoring teeth in need of restoration in a patient by providing a fluid dental restoration polymer composition which is curable on prepared teeth to be restored and curing the composition to provide the composition bonded to the prepared teeth in providing restored teeth, the improvement which comprises:
    (a) preparing selected teeth to be restored for bonding with the fluid polymer composition:
    (b) covering teeth which are not to be restored with a polymer release material;
    (c) fitting a clear polymer composition mold over the teeth to be restored and the teeth not to be restored, which mold provides a closed space to be filled between the teeth to be restored and the mold which defines a shape of the restored teeth, wherein the mold has an inlet port for injection of the fluid polymer composition and an outlet port for removing any excess air and excess fluid polymer resulting from the injection;
(d) injection molding the fluid polymer composition into the mold to fill the space in the mold with the covered teeth and the teeth to be restored;
(e) curing the fluid polymer composition onto the teeth to be restored in the clear polymer composition mold;
(f) removing the mold from the teeth and the tape from the covered teeth to provide the restored teeth in the patient.

23. The kit of claim 22 wherein the instructions call for restoration of alternate teeth to be restored in two or more of method steps (a) to (e).

\* \* \* \* \*

UNITED STATES PATENT AND TRADEMARK OFFICE
CERTIFICATE OF CORRECTION

| | | |
|---|---|---|
| PATENT NO. | : 7,217,131 B2 | Page 1 of 1 |
| APPLICATION NO. | : 10/998320 | |
| DATED | : May 15, 2007 | |
| INVENTOR(S) | : William C. Vuillemot | |

It is certified that error appears in the above-identified patent and that said Letters Patent is hereby corrected as shown below:

Column 12, line 6, "steps (a) to (e)" should be --steps (a) to (e) of Claim 1--.

Signed and Sealed this

Eighteenth Day of November, 2008

JON W. DUDAS
*Director of the United States Patent and Trademark Office*